United States Patent [19]

Suzuki

[11] Patent Number: 5,632,273
[45] Date of Patent: May 27, 1997

[54] METHOD AND MEANS FOR MEASUREMENT OF BIOCHEMICAL COMPONENTS

[75] Inventor: Susumu Suzuki, Hamamatsu, Japan

[73] Assignee: Hamamatsu Photonics K.K., Hamamatsu, Japan

[21] Appl. No.: 270,986

[22] Filed: Jul. 5, 1994

[30] Foreign Application Priority Data

Feb. 4, 1994 [JP] Japan .................................. 6-012653

[51] Int. Cl.$^6$ .................................................. A61B 5/00
[52] U.S. Cl. .................................................. 128/633; 356/39
[58] Field of Search ....................... 128/633, 664; 356/39, 40, 41

[56] References Cited

U.S. PATENT DOCUMENTS

| | | | |
|---|---|---|---|
| 4,796,636 | 1/1989 | Branstetter et al. | 128/633 |
| 5,057,695 | 10/1991 | Hirao et al. | 128/633 |
| 5,277,181 | 1/1994 | Mendelson et al. | 128/633 |
| 5,285,783 | 2/1994 | Secker | 128/633 |
| 5,297,548 | 3/1994 | Pologe | 128/633 |

OTHER PUBLICATIONS

Jacques, S.L. "Time–Resolved Reflectance Spectroscopy in Turbic Tissue", IEEE Transactions in BME, vol. 36, pp. 1155–1161, 1989.

*Primary Examiner*—Angela D. Sykes
*Assistant Examiner*—Eric F. Winakur
*Attorney, Agent, or Firm*—Stanger & Dreyfus, P.C.

[57] ABSTRACT

Biochemical components and changes in the components are measured by directing light of several wavelengths into a body at one location, sensing light at the wavelengths emerging from the body at a plurality of distances from the one location, and ascertaining biochemical component characteristics in the body as a function of variations, with respect to distance, of the logarithm of the ratio of the light sensed to the light directed into the body. The variations with respect to distance are in the form of the derivative and square of the derivatives of the logarithm.

28 Claims, 6 Drawing Sheets

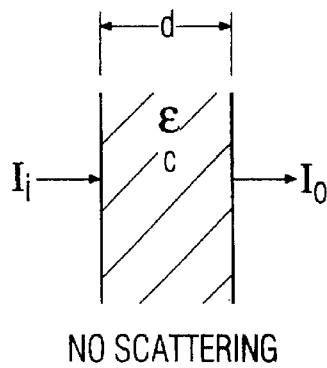

$OD = -\log(I_0 / I_i)$
$\quad\quad = \varepsilon cd$ $\varepsilon$ = MOLAR EXTINCTION COEFFICIENT
$c$ = CONCENTRATION
$d$ = DISTANCE

NO SCATTERING

FIG. 9

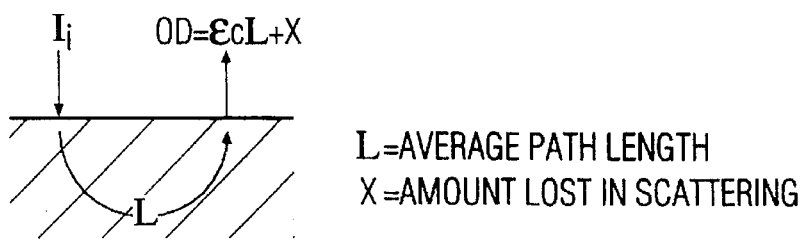

$L$ = AVERAGE PATH LENGTH
$X$ = AMOUNT LOST IN SCATTERING

FIG. 10

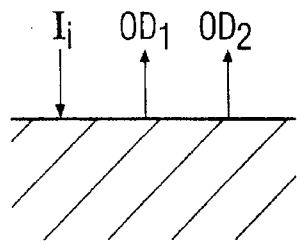

$\Delta d\overline{OD} = \overline{OD}_2 - \overline{OD}_1$
$\quad\quad = \varepsilon c \Delta dL$ $\Delta dL$ = DIFFERENCE OF LIGHT PATH LENGTH BETWEEN 2 POINTS.

FIG. 11

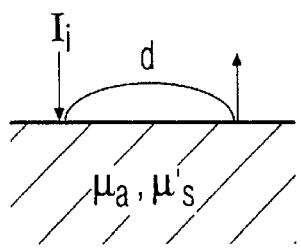

$\mu_a$ = LIGHT EXTINCTION COEFFICIENT (1/cm)

$\mu'_s$ = ACTUAL SCATTERING COEFFICIENT (1/cm)

$\begin{cases} \mu'_s \gg \mu_a \\ d \gg 1/\mu'_s \\ d \gg 1/\sqrt{3\mu_a\mu'_s} \end{cases}$ MEASUREMENT CONDITION ON REAL USE

FIG. 12

METHOD AND MEANS FOR MEASUREMENT OF BIOCHEMICAL COMPONENTS

FIELD OF THE INVENTION

This invention relates to methods and means for measurement of chemical components, and particularly to non-invasive measurement of biochemical components of a human or animal body.

BACKGROUND OF THE INVENTION

U.S. Pat. Nos. 4,281,645, 4,223,680, and 5,119,815 describe non-invasive measurement of biochemical components, such as hemoglobin (H), oxyhemoglobin (HbO$_2$), and cytochrome (CyOx) in a human or animal body. These systems introduce a beam of electromagnetic radiation in the form of infra-red light into the body at one point, sense the radiation emerging at another point, process the sensed data in a processor, and display or graph the results. U.S. Pat. No. 4,281,645 involves transillumination across the body from one point to an opposing point on the other side of the body. U.S. Pat. No. 4,223,680 discloses measuring along spaced parts of the body and using two detectors, one located near the light source to correct for light scattered from the skin. U.S. Pat. No. 5,119,815 entails using a pulsed light source.

These methods attempt to determine characteristics of such components on the basis of certain assumptions of the correlation between light intensities and the average light paths. However, it is believed that these assumptions lead to inaccuracies that arise from changes in the average light paths with changes in the concentration of the components.

An object of the invention is to improve prior art systems.

Another object is to overcome the aforementioned problems.

Still another object is to provide improved measurement optrode.

Yet another object is to provide a measurement system which permits accurate measurement of concentration of biochemical compounds.

SUMMARY OF THE INVENTION

According to a feature of the invention such results are achieved by directing electromagnetic radiation of several wavelengths into a body at one location, sensing electromagnetic radiation of the several wavelengths emerging from the body at a number of distances from the one location; and ascertaining biochemical component characteristics in the body as a function of variations, with respect to distance, of the negative logarithm of the ratio of the electromagnetic radiation at the wavelengths.

According to another feature of the invention, the variations with respect to distance are in the form of the derivative of the logarithm.

According to another feature of the invention, ascertaining includes determining concentrations of biochemical components as a function of the square of said variations.

According to another feature of the invention, includes determining concentrations of biochemical components as a function of the square of said variations, a scattering coefficient, and an extinction coefficient.

According to another feature of the invention, ascertaining includes determining concentrations of biochemical components as a function of the square of said derivative, and an absorption coefficient, composed of a scattering coefficient times an extinction coefficient.

According to yet another feature of the invention, each of the steps or functions above are performed by means for performing them.

BRIEF DESCRIPTION OF THE DRAWINGS

FIG. 9 is a diagram illustrating the passage of light from one face to an opposite face, without optical scattering, and the optical density resulting therefrom.

FIG. 10 is a section of the average path length of light path between two points along a face when light is subject to optical scattering.

FIG. 11 is a graph of the variation of optical density at different distances from the light source along a face.

FIG. 12 is a diagram of the absorption coefficient and actual scattering coefficient using the device in FIGS. 1 to 4.

DETAILED DESCRIPTION OF PREFERRED EMBODIMENTS

Figure 1:
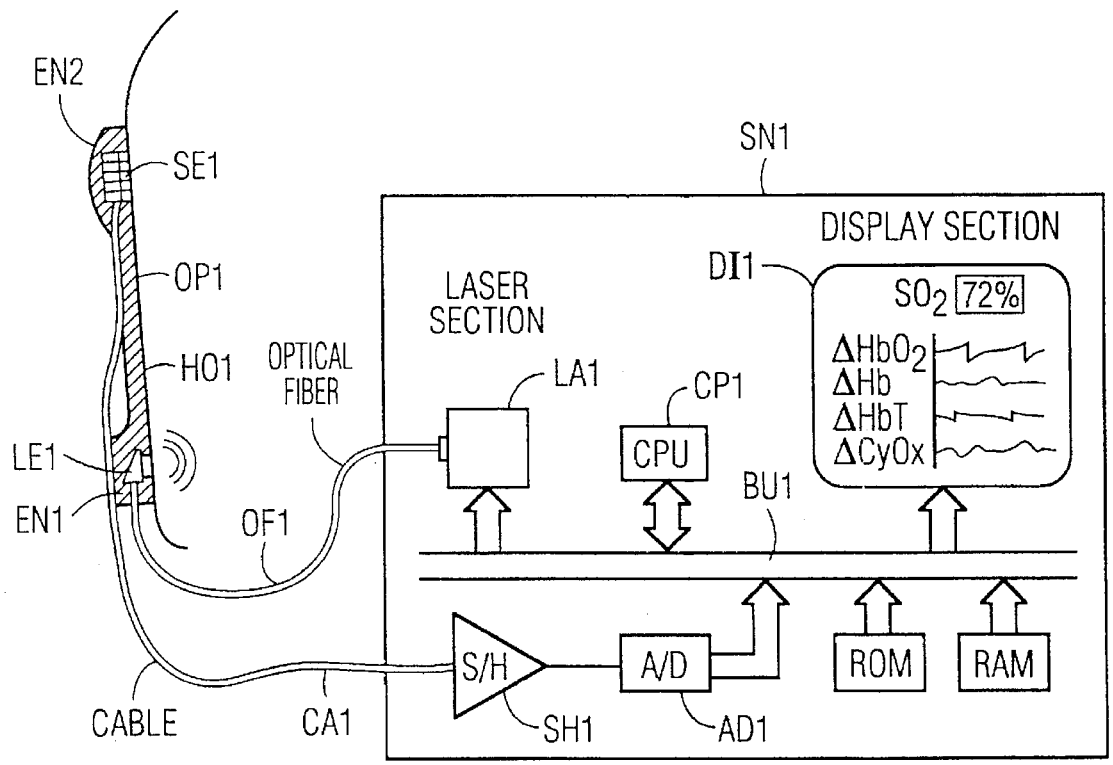
FIG. 1 is a partial elevation and block diagram of a device embodying features of the invention.
Figure 2:
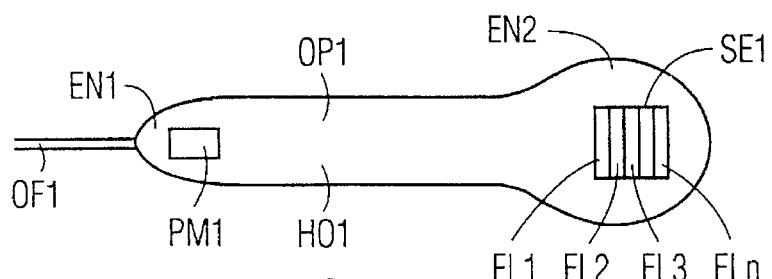
FIG. 2 is a plan of a device in FIG. 1 for emitting and sensing light.
Figure 3:
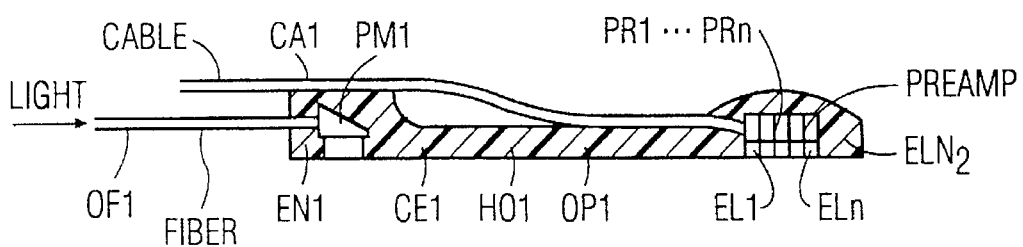
FIG. 3 is an elevation of FIG. 2.

FIG. 1 illustrates a system embodying the invention. Here, an optrode OP1 connects to a processing and display section SN1 via a cable CA1 and an optical fiber OF1. Details of the optrode OP1 appear in the plan view thereof of FIG. 2, the elevational section of FIG. 3, and the perspective view as placed on a human head in FIG. 4. In the optrode OP1 an elongated, flexible, silicone rubber, holder HO1 carries a light emitter LE1 at one end EN1, and an optical sensor SE1 at another wider end EN2. The holder HO1 spaces the light emitter LE1 about 5 cm away from the sensor SE1. The holder HO1 is thickened at the ends EN1 and EN2 to accommodate the light emitter LE1 and the other end EN2 to accommodate the sensor SE1, while the central portion CE1 between the ends is kept thin to maintain flexibility.

The emitter LE1 takes the form of a triangular-crosssectioned prism PM1 which receives light at one face FA1 from the optical fiber OF1. The latter extends, at the prism, in the elongated direction of the optrode OP1. The fiber OF1 receives its light from the section SN1. The prism PM1 internally reflects the light from the fiber OF1 vertically downward in FIG. 3 and transverse to the surface of the head and into the head in FIG. 4. The sensor SE1 is a photo-diode array of n photodiode elements EL1 to ELn aligned in the direction of light entering the prism PM1 of the emitter EM1 from the fiber OF1. The sensor SE1 is a linear sensor and senses light emerging from the head HE1. The sensor SE1 includes n preamplifiers PR1 to PRn, one for each element ELn. Each preamplifier PR1 to PRn accumulates electrons from a corresponding photodiode element ELn and amplifies them. The preamplifiers PR1 to PRn can detect low level signals with good sensitivity and send the detected signals to the section SN1.

Figure 4:
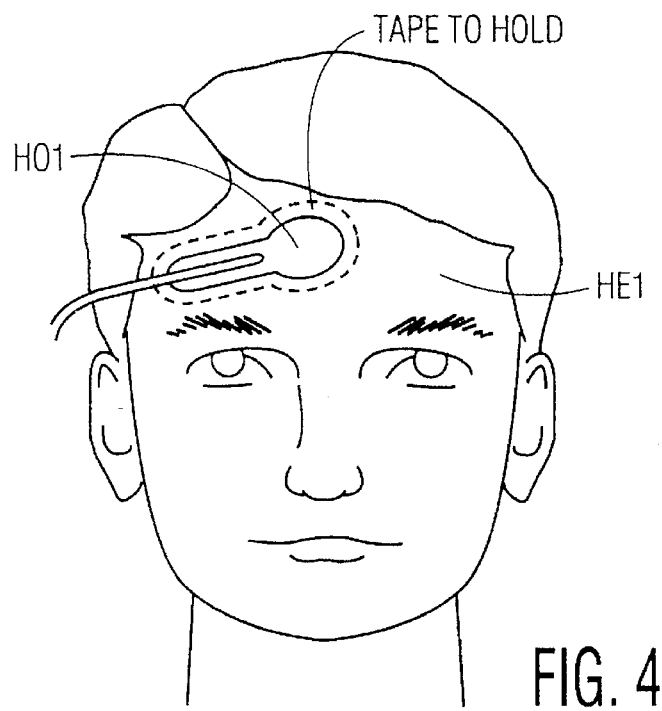
FIG. 4 is a diagram of the device of FIG. 1 and 2 as used on the head of a patient.

In FIG. 4 tape or a flexible bandage attaches the optrode OP1 to the head where it is clinically important to know Hb, HbO, CyOx. For convenience, the optrode is attached at a location without hair. Attachment to the head is only an example. The optrode may be used on other parts of the body.

Figure 5:
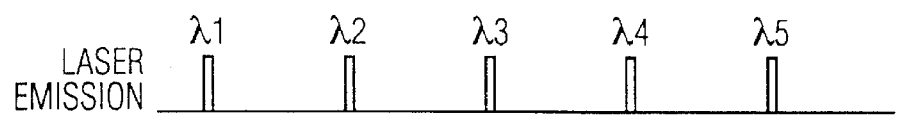
FIG. 5 is a graph illustrating the emission of light from the device of FIGS. 1 to 4.

In FIG. 1, the section SN1 contains a solid state laser arrangement LA1 which emits repeated cycles of pulses. In each cycle, the laser arrangement LA1 sequentially emits five pulses of light at different wavelengths $\lambda_i$, where i=1,2,3,4, and 5 (hence $\lambda_1$, $\lambda_2$, $\lambda_3$, $\lambda_4$, and $\lambda_5$). One cycle of pulses appears in FIG. 5. The light from the laser arrangement LA1 passes through the optical fiber OF1, to the prism PM1 which refracts the light 90 degrees so it is directed transverse to the surface of the head HE1. There it is introduced into the human body.

Figure 6:
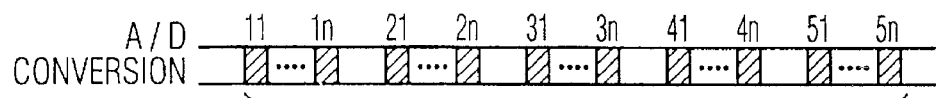
FIG. 6 is a graph showing the A/D conversion of the graph in FIG. 5.
Figure 7:
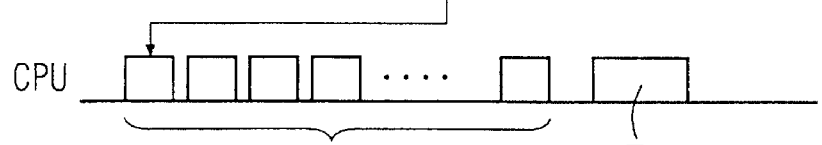
FIG. 7 is a graph of data accumulated from the information in FIG. 6.

After the light passes into the human body, each of the n elements EL1 to ELn of the sensor SE1 senses each of the i pulses per cycle and the preamplifiers PR1 to PRn transmit the sensed pulses to a sample and hold array SH1 of n sample and hold circuits. An analog to digital converter AD1 digitizes each sampled and held value as shown in the diagram of FIG. 6 and applies it via a bus BU1 to a central processing unit (CPU) CP1 which accumulates and processes the data as shown by the graph of FIG. 7. A read only memory (ROM) RO1 and a random access memory (RAM) RA1 provide required memory for the CPU CP1. A display DI1 displays the output of the CPU CP1 in values of delta $HbO_2$, Hb, HbT, CyOx, etc.

Figure 8:
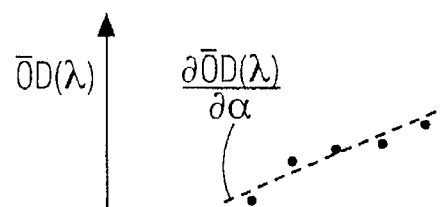
FIG. 8 is a graph illustrating the variations in optical density at different distances from a light source in the device of FIGS. 1 to 4.

Analog to digital conversion by the converter AD1 and processing by the CPU CP1 of one cycle of 5 pulses takes about 1 millisecond. The CPU CP1 integrates about 1000 cycles per second. Because the signal obtained by a single emission of light is comparatively weak the CPU CP1 accumulates the data from 5 to 10 seconds, namely for 5,000 to 10,000 cycles. When this accumulation ends, the CPU CP1 performs a log conversion of the data for each wavelength and each pixel and calculates the optical density OD where $$OD = -\log(I_o/I_i),$$

where $I_o$ is sensed intensity, and $I_i$ is the input intensity. As shown in FIG. 8 it uses the OD from each sensor SE1 to calculate $$\frac{\partial OD(\lambda_i)}{\partial d}$$

for each wavelength, $\lambda i$ where d is the distance from the light source.

The CPU CP1 then calculates and displays the Oxyhemoglobin saturation ratio $SO_2(\%)$ and the concentrations of Oxyhemoglobin $HbO_2$, Hemoglobin Hb, Cytochrome CyOx, changes in concentration of the $HbO_2$, Hb, CyOx. The Oxyhemoglobin saturation ratio=$HbO_2/(HbO_2+Hb)$ Any or all of these values are also graphed as a function of time to indicate trends.

The basis for the operation of the CPU CP1 is described with respect to FIGS. 9 to 12. The operation of the CPU CP1 appears in the flow chart of FIGS. 13 to 15.

The invention is based on the Beer-Lambert law, illustrated in FIG. 9. When light passes through an absorbing medium under conditions of no light scattering the light absorption or optical density OD, i.e. the change in light intensity $-\log(I_o/I_i)$, is proportional or equal to the product $\epsilon cd$ of a known molar extinction coefficient $\epsilon$, the concentration c of the absorption pigment, and distance d. When there is light scattering, the modification of Beer-Lambert law, $$OD = \epsilon cL + X \tag{1}$$

has been used as shown in FIG. 10, where L is average light path distance between the position of input light and detecting position, X is the contribution of light which is not picked by detector due to the scattering. Since X is unknown, Equation 1 is unsuitable for accurate measurements. Prior art systems used $$\Delta(OD)_t = \epsilon L \Delta(C)_t \tag{2}$$

for determining only temporal variation of light absorbance, $\Delta(OD)_t$, or measured the concentration variation of each compound or the variation of the Oxygen saturation ratio of Hemoglobin by measuring the difference of OD at two points as shown in FIG. 11, and by using the relation $$\Delta(OD)_d = \epsilon L \Delta(L)_d \tag{3}$$

These equations assume that the average light path length L is constant. But in reality, L varies depending on the light extinction coefficient $\mu_a$ ($\mu_a = \Sigma \epsilon_i c_i$) where $\mu_a$ is in units of 1/cm. For example, when the absorption increases, the light that travels along a longer trajectory before it reaches the detector is attenuated more than light that travels along a shorter trajectory. Thus the contribution of the detected signal arising from the shorter path is increased relative to the light along the longer path. As result, L becomes shorter, since L is a weighted average of all paths that go to the detector. On the other hand, if the absorption is decreased, L becomes longer. Therefore the light absorption OD is not proportional to the concentration c, and equations 2 and 3 represent broad approximations that can lead to errors.

In general, the behavior of light inside an organism can be approximated as a scattering phenomenon, with a diffusion coefficient. $D = \{3(\mu_a + \mu'_s)\}^{-1}$, where $\mu'_s$ is the actual scattering coefficient in units of 1/cm. In FIG. 12, light is injected at one point and detected a distance d away. In general, $\mu'_s \gg \mu_a$, $d > 1/\mu'_s$, $d > 1/\sqrt{3\mu_a\mu'_s}$. For the sake of simplicity the injected light is a pulse of very short duration. Scatter through the organism results in an output of the following response function at distance d:

$$R(d, t) = \left(\frac{4\pi C}{3\mu_s'}\right)^{-\frac{3}{2}} \frac{1}{\mu_s'} t^{-\frac{5}{2}} \exp(-\mu_a ct) \exp\left(-\frac{3\mu_s' d^2}{4ct}\right) \tag{4}$$

where the detected photon quantity I(d) is the time-integrated value of the response function. Then, $$I(d) = \int_0^\infty R(d, t)dt = A(\mu_a, \mu_s')d^{-2}\exp(-d\sqrt{3\mu_a\mu_s'}) \tag{5}$$

Since light absorption quantity OD(d) is the minus or negative logarithm of detected light quantity I(d), $$OD(d) = -\log I(d) = +\frac{1}{\ln 10} [d\sqrt{3\mu_a\mu_s'} + 2\ln d] - \ln A(\mu_a, \mu_s')$$

(Ordinarily OD is estimated by $OD=\mu_a L+X$ where ($\mu_a=\epsilon c$)). The invention simplifies the complex relationship between OD and $\mu_a$ in the last equation for OD(d) by taking the derivative $$\left(\frac{\partial OD}{\partial d}\right).$$

$$\frac{\partial OD}{\partial d} = \frac{\sqrt{3\mu_a\mu_s'}}{\ln 10} + \frac{2}{d\ln 10} \quad (7)$$

Here, the first term is independent of d, when the second term decreases as d increases. For example, using the typical values, $\mu_a\mu_s' \approx 0.1$ mm$^{-2}$, d>40 mm, the second term becomes less than one tenth of the first term and can be approximately by the first term. Therefore:

$$\frac{\partial OD}{\partial d} \approx \frac{\sqrt{3\mu_a\mu_s'}}{\ln 10} \text{ or } \left(\frac{\partial \overline{OD}}{\partial d}\right)^2 \approx \frac{3\mu_s'}{\ln^2 10} \mu_a \quad (8)$$

Thus CPU CP1 employs the latter equation to calculate the concentration of each biochemical j by acquiring $$\frac{\partial OD(\lambda_i)}{\partial d}$$

with multiple wavelengths $\lambda i$ using the optrode OP1 and the matrix formula:

$$\mu_{ai} = \sum_j \epsilon_j(\lambda_i) C_j \text{ (}j = \text{each of } j \text{ components)}. \quad (9)$$

$(i = 1 \ldots N)$ where $\mu_{ai}$ is for the wavelength $\lambda i$ and N is at least equal to the number of compounds determined plus 1 for a baseline.

The coefficient $$\frac{3\mu_s'}{\ln^2 10}$$

that multiples $\mu_a$ is independent of $\mu_a$. Consequently, the linear dependence of $$\left(\frac{\partial \overline{OD}}{\partial d}\right)^2$$

on $\mu_a$ is maintained. Precise measurement of $\mu_a$ is possible. The value $\mu'_s$, over the appropriate wavelength range can be considered constant.

The CPU CP1 measures the biochemical substances HbO$_2$, Hb, CyOx, H2O, as well as a baseline where these compounds do not absorb, using the matrix:

$$\begin{bmatrix} \left(\frac{\partial OD(\lambda_1)}{\partial d}\right)^2 \\ \vdots \\ \left(\frac{\partial OD(\lambda_n)}{\partial d}\right)^2 \end{bmatrix} = \begin{bmatrix} \epsilon_{HbO2}(\lambda_1) & \cdots & \epsilon_{PH2O}(\lambda_1), 1 \\ \vdots & & \vdots \\ \epsilon_{HbO2}(\lambda_5) & \cdots & \epsilon_{H2O}(\lambda_5), 1 \end{bmatrix} \begin{bmatrix} KC_{HbO2} \\ KC_{Hb} \\ KC_{CyOx} \\ KC_{H2O} \\ KC_{off} \end{bmatrix} \quad (10)$$

Here, $K = \frac{3\mu_s'}{\ln^2 10}$.

The CPU CP1 acquires the relative concentration of each compound j, KCj, by using the aforementioned matrix equation.

The CPU CP1 then calculates Hemoglobin Oxygen saturation $$\frac{KC_{Hb}}{KC_{HbO_2} + KC_{Hb}}$$

which is clinically significant. According to the above method, the CPU CP1 obtains the relative density of all the elements.

The measurement accuracy for low concentration CyOx involves a calculation based on the temporal change in $$\left(\frac{\partial OD}{\partial d}\right)^2.$$

The value $$\left(\frac{\partial OD}{\partial d}\right)^2$$

itself includes the absorbance of all the compounds. Therefore solving equation 10 involves including the absorbance of water as well as the baseline contributions from all other substances that absorb in the wavelength range of the measurement.

On the other hand, in case of $\Delta_t$ $$\left(\frac{\partial OD}{\partial d}\right)^2,$$

when solving the equation while considering only the element which varies during measurement, HbO$_2$, Hb, CyOx, there is no need to consider the influence of things like Offset. The accuracy is greatly improved (even though what is measured is a variation of concentration K$\Delta$C). To be precise, CPU CP1 uses the following formula to obtain values of changes with respect to time in concentrations of HbO$_2$, Hb, and CyOx.

$$\begin{bmatrix} \Delta t \left(\frac{\partial OD(\lambda_1)}{\partial d}\right)^2 \\ \Delta t \left(\frac{\partial OD(\lambda_2)}{\partial d}\right)^2 \\ \vdots \\ \Delta t \left(\frac{\partial OD(\lambda_n)}{\partial d}\right)^2 \end{bmatrix} = \begin{bmatrix} \epsilon_{HbO2}(\lambda_1) & \cdots & \cdots \\ \vdots & \cdots & \cdots \\ \cdots & \cdots & \epsilon_{CyOx}(\lambda_n) \end{bmatrix} \begin{bmatrix} K\Delta_t C_{HbO2} \\ K\Delta_t C_{Hb} \\ K\Delta_t C_{CyOx} \end{bmatrix} \quad (11)$$

For measurement value of CyOx, the CPU CP1 obtains the variation of the concentration from matrix equation (11). For Hb and HbO$_2$, it compares the variation of $KC_{HbO2}$, $KC_{Hb}$ in the matrix equation (10) and determines $K\Delta_i C_{HbO2}$, $K\Delta CHb$ from matrix equation (11). If these are almost the same, it supports the validity of the Hemoglobin concentration calculated by the former of the two matrix equations.

As shown above, by measuring $$\left( \frac{\partial OD}{\partial d} \right)^2,$$

the error generated by $\mu_a$ dependence of path length for the current method, which uses OD from equations 1,2, or 3, is improved. The measurement accuracy and reliability also increased by measuring the change of concentration with time, by determining $$\Delta_t \left( \frac{\partial OD}{\partial d} \right)^2.$$

Figure 13:
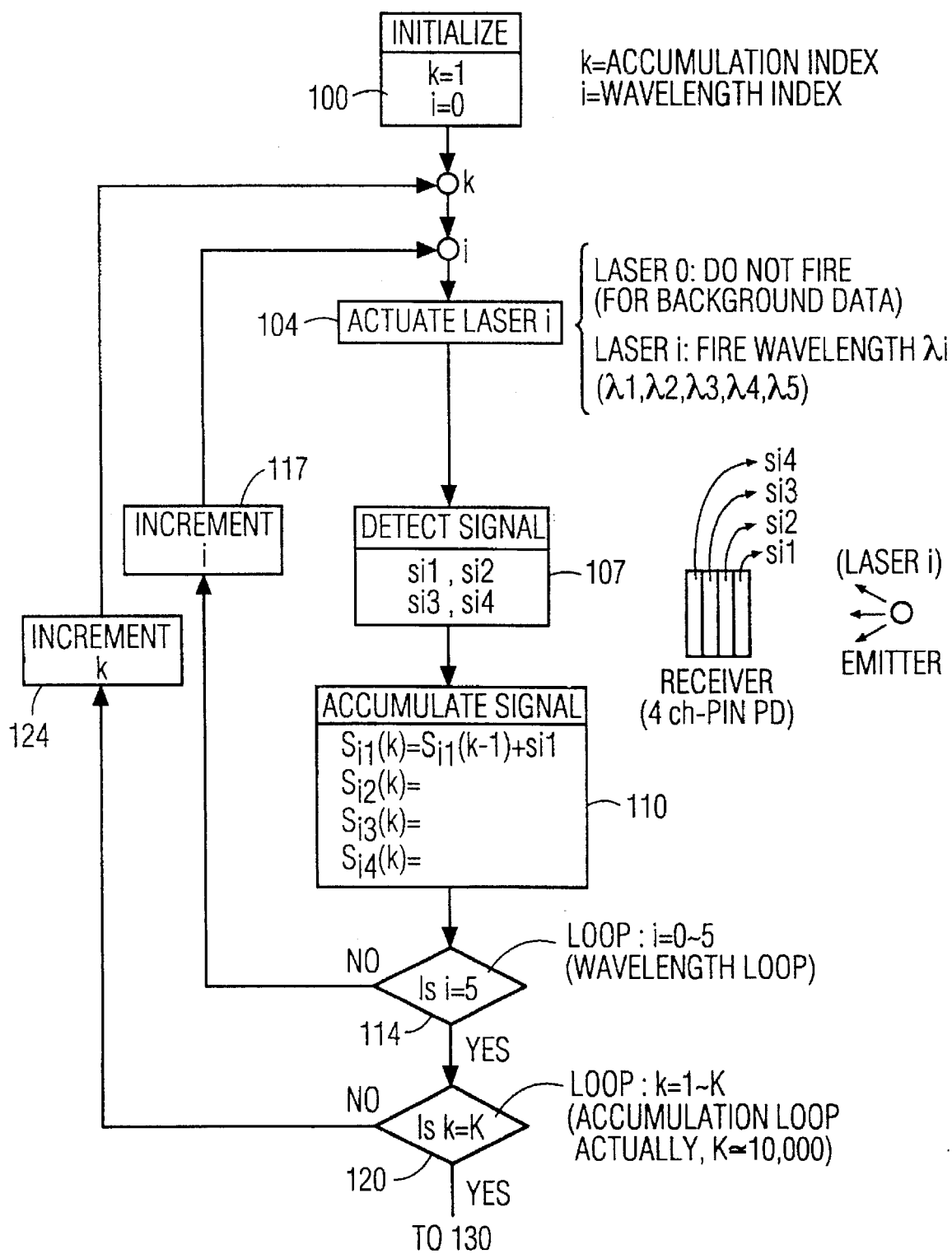
FIGS. 13, 14, and 15 are flow charts illustrating operation of the system in FIG. 4.
Figure 14:
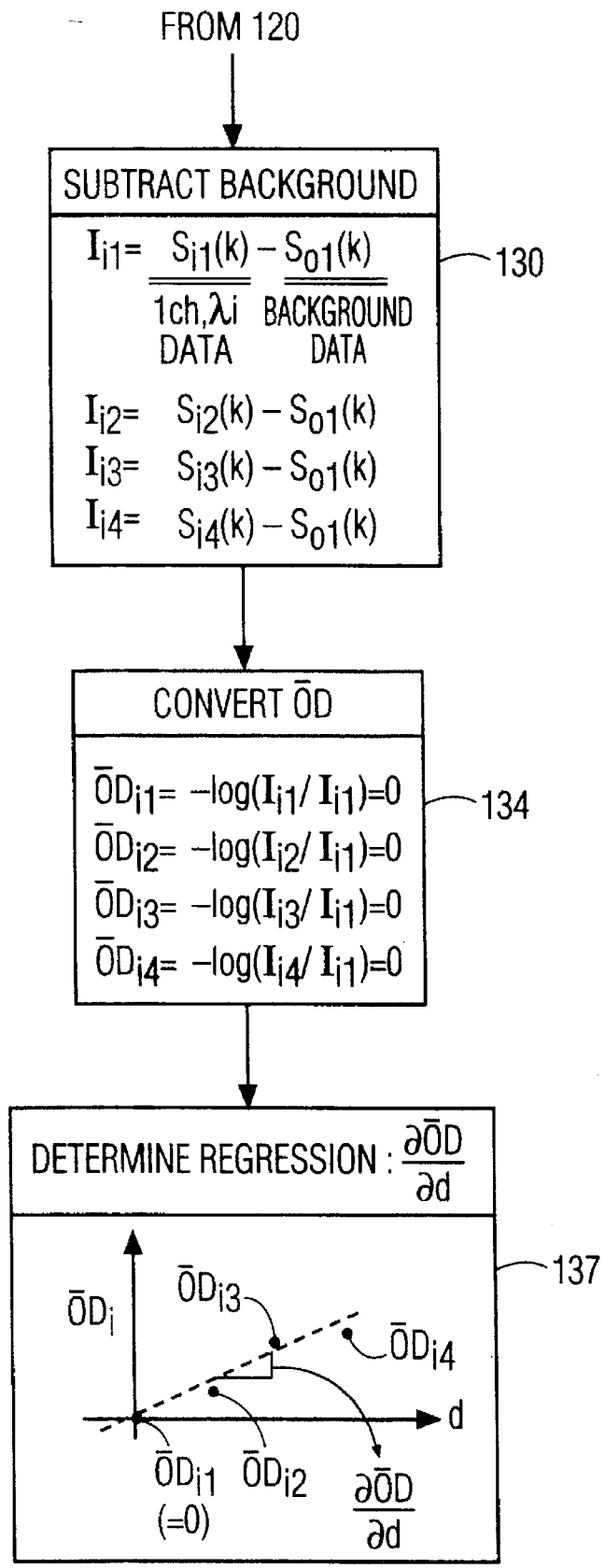
Figure 15:
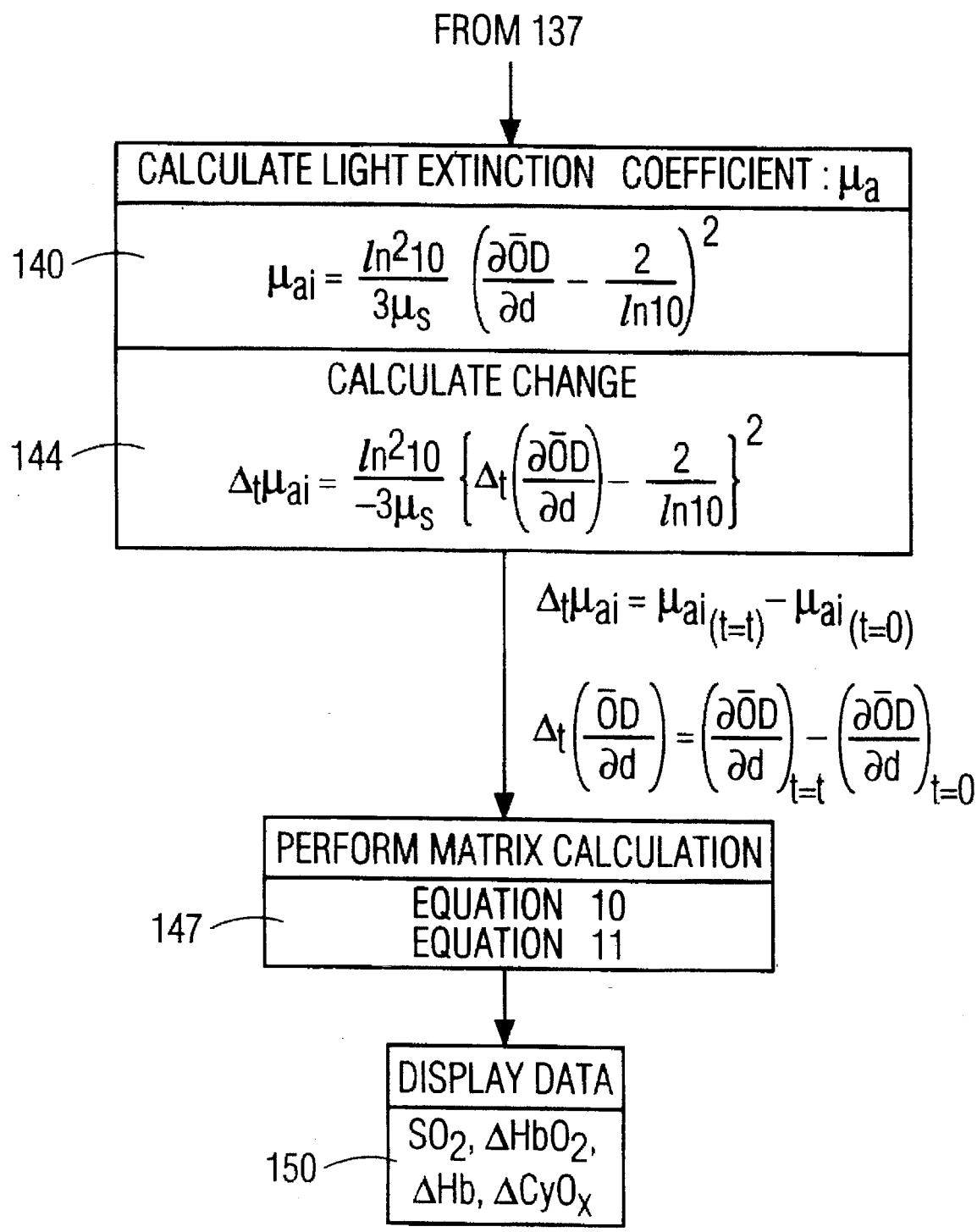

The system operates as shown in the flow chart of FIGS. 13, 14, and 15. In step 100, the CPU CP1 initializes an accumulation index k=1, and a wavelength index i=0. It then passes to step 104 to actuate laser 0. Such actuation does not actually occur, because there is no laser 0. The step leaves a time slot for detection of background noise. Without a signal from the lasers the fiber OF1 carries no light and the prism PM1 emits no light. However in step 107, the sensor SE1 senses signals $s_{i1}$, $s_{i2}$, $s_{i3}$, and $s_{i4}$ representing background noise. The preamplifiers PR1 to PRn transmit the signals via the cable CA1 to the sample and hold circuits SH1 to SHn, to the converters AD1, and to the CPU CP1. In step 110, the CPU CP1 accumulates this signal with all previous signals if any.

In step 114, the CPU asks whether i=5. If not, the process advances to step 117 to increment i and returns to step 104 to fire laser 1. At step 107 the sensor SE1 detects signals $s_{i1}$, $s_{i2}$, $s_{i3}$, and $s_{i4}$ from firing of laser 1. In step 110 the sensed signals are accumulated with previously sensed signals. The loop through step 117 repeats until i=5. This then completes one cycle.

When i=5 at step 114, the CPU CP1 progresses to step 120 which asks whether k=K (K typically equals 10,000). If not, the system goes on to step 124 to increment k. Such incremental advance occurs once each cycle of i. For each increment of k a new cycle begins for i=0, 1, 2, . . . 5.

When k=K, the process goes on to step 130. Here, the CPU CP1 subtracts all background data $S_{o1(k)}$ from each 1ch, $\lambda_i$ data $S_{i1(k)}$, $S_{i2(k)}$, $S_{i3(k)}$, and $S_{i4(k)}$ to obtain values of detected light quantities $I_{i1}$, $I_{i2}$, $I_{i3}$, and $I_{i4}$. The relationship between the detected light quantities $I_i$ and the light absorption quantity OD is that the light absorption quantity OD(d) is a minus logarithm of the detected light quantity I(d). Hence, OD(d)=-log I(d), and $OD_i$=-log $(I_i/I_{(i-1)})$. In step 134 the CPU CP1 converts these values to values of light absorption changes OD along the separation, where $$\Delta \bar{O}D_{i1} = -\log(I_{i1}/I_{i1}) = 0$$
$$\Delta \bar{O}D_{i2} = -\log(I_{i2}/I_{i1})$$
$$\Delta \bar{O}D_{i3} = -\log(I_{i3}/I_{i1})$$
$$\Delta \bar{O}D_{i4} = -\log(I_{i4}/I_{i1})$$

The CPU CP1 now determines regression $\partial \bar{O}D/\partial d$ in step 137. In step 140 it calculates the extinction coefficient $\mu_a$ for each i. In step 144 it calculates the change in extinction coefficient $\Delta_t \mu_a$, where $$\Delta_t \mu_a = (\mu_{ai})_{(t=t)} - (\mu_{ai})_{(t=0)} \tag{12}$$

The CPU CP1 now performs the matrix calculation in step 147 and, in step 150, displays the data for $SO_2$, $\Delta HbO_2$, $\Delta Hb$, $\Delta CyOx$.

According to an embodiment of the invention, laser diodes or LEDs replace the prism PM1, and a cable for energizing the laser diodes or LEDs replaces the optical fiber OF1.

The invention permits accurate measurement of concentrations and changes in concentrations of biochemical compounds.

Sample values of the known extinction coefficient ε are shown for various wavelengths in the following table:

TABLE 1

| Wavelength (mm) | Hb ($mM^{-1}cm^{-1}$) | $HbO_2$ ($mM^{-1}cm^{-1}$) | CytOx ($mM^{-1}cm^{-1}$) |
|---|---|---|---|
| 800 | 0.8399 | 0.8653 | 2.2619 |
| 801 | 0.8338 | 0.8716 | 2.2666 |
| 802 | 0.8285 | 0.8780 | 2.2713 |
| 803 | 0.8237 | 0.8845 | 2.2762 |
| 804 | 0.8190 | 0.8909 | 2.2812 |
| 805 | 0.8146 | 0.8973 | 2.2870 |
| 806 | 0.8111 | 0.9038 | 2.2927 |
| 807 | 0.8075 | 0.9102 | 2.2991 |

According to an embodiment of the invention, the processor CPU CP1 calculates values of C by the linear least squares method. To start, the measured concentrations are plural (C1,C2, . . . ,Cj) and the general form of equation 10 contains n wavelengths and j components (n≧j) and is $$\begin{bmatrix} \left( \frac{\partial \bar{O}D(\lambda_1)}{\partial d} \right)^2 \\ \cdot \\ \cdot \\ \left( \frac{\partial \bar{O}D(\lambda_n)}{\partial d} \right)^2 \end{bmatrix} = \begin{bmatrix} \epsilon_1(\lambda_1) \ldots \epsilon_j(\lambda_1) \\ \cdot \\ \cdot \\ \epsilon_1(\lambda_n) \ldots \epsilon_j(\lambda_n) \end{bmatrix} \begin{bmatrix} KC_1 \\ \cdot \\ \cdot \\ KC_j \end{bmatrix} \tag{13}$$

At the left is (n×1)matrix OD. Then (n×j)matrix ε, and (j×1)matrix KC.

The general form of the equation, in the next matrix form, is:

$$\phi D = \phi . K \phi$$

where "." is matrix multiplication then, where, $K_\phi = \phi^*$. $\phi B \phi^* = (\phi^T . \phi)^{-1} . \phi^T$. Here, $\phi^T$: Transpose matrix, $\phi^{-1}$: square inverse matrix, and (j-n) matrix $\phi^*$ is the pseudo-inverse matrix of $\phi$.

The value $$K \left( = \frac{3\mu s}{\ln^2 10} \right)$$

is given by other measurements. Thus the processor CPU CP1 obtains C itself by this linear least squares method in step 147.

The laser LA1 and the prism PM direct the wavelengths in a pulse or sine wave form.

While embodiments of the invention have been described in detail, it will be evident to those skilled in the art that the invention may be embodied otherwise without departing from its spirit and scope.

What is claimed is:

1. The method, comprising:
   directing electromagnetic radiation at one or more wavelengths into a body at one location;
   sensing electromagnetic radiation at the wavelengths emerging from the body at a plurality of distances from the one location; and ascertaining biochemical component characteristics in the body as a function of differences in a negative logarithm of the electromagnetic radiation sensed for the wavelengths at the plurality of distances, and a scattering coefficient relative to the wavelengths at each of the distances.

2. The method as in claim 1, wherein the differences with respect to distance are in a form of the derivative of the negative logarithm.

3. The method as in claim 2, wherein the step of ascertaining further includes determining concentrations of biochemical components as a function of the square of said derivative, and a molar extinction coefficient.

4. The method as in claim 3, wherein the sensing is performed on a number of elements j by a plurality of detectors each at one of the plurality of distances, and wherein the step of determining includes calculating a concentration $C_j$ each of the elements j on the basis of equation $$\frac{\partial OD}{\partial d} = \frac{\sqrt{3\mu_a\mu_s'}}{\ln 10} + \frac{2}{d \ln 10}$$

where $\mu_a = \sum_j c_j \epsilon_j$, and $OD = -\log(I_o/I_i)$, $\mu_a$ is an extinction coefficient, $\mu'_s$ is a scattering coefficient, and $\epsilon_j$ is a known molar extinction coefficient for each of the elements j.

5. The method as in claim 3, wherein the sensing is performed on a number of elements j by a plurality of detectors each at one of the plurality of distances, and wherein the step of determining includes calculating a concentration $C_j$ for each of the elements j on the basis of equation $$\frac{\partial OD}{\partial d} \approx \frac{\sqrt{2\mu_a\mu_s'}}{\ln 10} \text{ or } \left(\frac{\partial \overline{OD}}{\partial d}\right)^2 \approx \frac{3\mu_s'}{\ln^2 10} \mu_a$$

where $\mu_a = \sum_j c_j \epsilon_j$, and $OD = -\log(I_o/I_i)$, $\mu_a$ = an extinction coefficient, $\mu_a$ is an extinction coefficient, $\mu'_s$ is a scattering coefficient, and $\epsilon_j$ is a known molar extinction coefficient for each of the elements j.

6. The method as in claim 5, wherein the step of calculating includes using the matrix formula $$\mu_{ai} = \sum_j c_j \epsilon_j(\lambda_i), (j = \text{each element}) (i = 1 \ldots N)$$

where $\mu_{ai}$ is for the wavelength $\lambda i$ and N is at least equal to a number of compounds determined plus 1 for a baseline.

7. The method as in claim 3, wherein the step of determining includes calculating concentrations from the matrix $$\begin{bmatrix} \left(\frac{\partial \overline{OD}(\lambda_1)}{\partial d}\right)^2 \\ \vdots \\ \left(\frac{\partial \overline{OD}(\lambda_n)}{\partial d}\right)^2 \end{bmatrix} = \begin{bmatrix} \epsilon_{HbO2}(\lambda_1) & \ldots & \epsilon_{H2O}(\lambda_1), 1 \\ \vdots & & \vdots \\ \epsilon_{HbO2}(\lambda_5) & \ldots & \epsilon_{H2O}(\lambda_5), 1 \end{bmatrix} \begin{bmatrix} KC_{HbO2} \\ KC_{Hb} \\ KC_{CyOx} \\ KC_{H2O} \\ KC_{off} \end{bmatrix}$$

where $K = \frac{3\mu_s'}{\ln^2 10}$.

8. The method as in claim 3, wherein the step of determining includes calculating concentrations from the matrix $$\begin{bmatrix} \left(\frac{\partial \overline{OD}(\lambda_1)}{\partial d}\right)^2 \\ \vdots \\ \left(\frac{\partial \overline{OD}(\lambda_n)}{\partial d}\right)^2 \end{bmatrix} = \begin{bmatrix} \epsilon_{HbO2}(\lambda_1) & \ldots & \epsilon_{H2O}(\lambda_1), 1 \\ \vdots & & \vdots \\ \epsilon_{HbO2}(\lambda_n) & \ldots & \epsilon_{H2O}(\lambda_n), 1 \end{bmatrix} \begin{bmatrix} KC_{HbO2} \\ KC_{Hb} \\ KC_{CyOx} \\ KC_{H2O} \\ KC_{off} \end{bmatrix}$$

where $K = \frac{3\mu_s'}{\ln^2 10}$.

and calculating changes in concentration from the matrix $$\begin{bmatrix} \Delta t \left(\frac{\partial OD(\lambda_1)}{\partial d}\right)^2 \\ \Delta t \left(\frac{\partial OD(\lambda_2)}{\partial d}\right)^2 \\ \vdots \\ \Delta t \left(\frac{\partial OD(\lambda_n)}{\partial d}\right)^2 \end{bmatrix} = \begin{bmatrix} \epsilon_{HbO2}(\lambda_1) & \ldots & \ldots \\ \ldots & \ldots & \ldots \\ \ldots & \ldots & \epsilon_{CyOx}(\lambda_n) \end{bmatrix} \begin{bmatrix} K\Delta_t C_{HbO2} \\ K\Delta_t C_{Hb} \\ K\Delta_t C_{CyOx} \end{bmatrix}.$$

9. The method as in claim 2, wherein the step of ascertaining further includes determining changes, with respect to time, of concentrations of biochemical components as a function of changes in time of the square of said derivative, and a molar extinction coefficient.

10. The method as in claim 9, wherein the step of determining includes calculating changes in concentrations from the matrix $$\begin{bmatrix} \Delta t \left(\frac{\partial OD(\lambda_1)}{\partial d}\right)^2 \\ \Delta t \left(\frac{\partial OD(\lambda_2)}{\partial d}\right)^2 \\ \vdots \\ \Delta t \left(\frac{\partial OD(\lambda_n)}{\partial d}\right)^2 \end{bmatrix} = \begin{bmatrix} \epsilon_{HbO2}(\lambda_1) & \ldots & \ldots \\ \ldots & \ldots & \ldots \\ \ldots & \ldots & \epsilon_{CyOx}(\lambda_n) \end{bmatrix} \begin{bmatrix} K\Delta_t C_{HbO2} \\ K\Delta_t C_{Hb} \\ K\Delta_t C_{CyOx} \end{bmatrix}$$

where $K = \frac{3\mu_s'}{\ln^2 10}$.

11. The method as in claim 1, wherein the step of ascertaining further includes determining concentrations of biochemical components as a function of the square of said differences.

12. The method as in claim 1, wherein the step of ascertaining further includes determining concentrations of biochemical components as a function of the square of said differences and a molar extinction coefficient.

13. The method as in claim 1, wherein the step of ascertaining further includes determining changes, with respect to time, of concentrations of biochemical components as a function of changes in time of the square of said differences and a molar extinction coefficient.

14. The method as in claim 1, wherein the step of directing directs the radiation at each wavelength in an impulse or sine wave form.

15. An apparatus, comprising:
means for directing electromagnetic radiation at one or more wavelengths into a body at one location;
means for sensing electromagnetic radiation at the plurality of wavelengths emerging from the body at a plurality of distances from the one location; and
means for ascertaining biochemical component characteristics in the body as a function of differences in a negative logarithm of the electromagnetic radiation sensed for the wavelengths at the plurality of distances, and a scattering coefficient relative to the wavelengths at each of the distances.

16. The apparatus as in claim 15, wherein, in the means for ascertaining, the differences with respect to distance are in the form of a derivative of the negative logarithm for the wavelengths.

17. The apparatus as in claim 16, wherein the means for ascertaining includes means for determining concentrations of biochemical components as a function of the square of said derivative, and a molar extinction coefficient.

18. The apparatus as in claim 17, wherein the means for sensing includes a plurality of detectors each for one of elements j and each at one of the distances, and wherein the means for determining includes means for calculating a concentration $c_j$ for each of the elements j on the basis of equation $$\frac{\partial OD}{\partial d} = \frac{\sqrt{3\mu_a\mu_s'}}{\ln 10} + \frac{2}{d\ln 10}$$

where $\mu_a = \sum_j c_j \epsilon_j$, where $OD = -\log(I_o/I_i)$, $\mu_a$ is an extinction coefficient, $\mu'_s$ is a scattering coefficient, and $\epsilon_j$ is a known molar extinction coefficient of the element j.

19. The apparatus as in claim 17, wherein the means for sensing includes a plurality of detectors each for one of elements j and each at one of the distances, and wherein the means for determining includes means for calculating a concentration $C_j$ for each of the elements j on the basis of equation $$\frac{\partial OD}{\partial d} \approx \frac{\sqrt{3\mu_a\mu_s'}}{\ln 10} \text{ or } \left(\frac{\partial \overline{OD}}{\partial d}\right)^2 \approx \frac{3\mu_s'}{\ln^2 10}\mu_a$$

where $\mu_a = \sum_j c_j \epsilon_j$, and $OD = -\log(I_o/I_i)$, $\epsilon_j$ is a known molar extinction coefficient for each of the elements j, $\mu_a$ is an extinction coefficient, and $\mu'_s$ is a scattering coefficient.

20. The apparatus as in claim 19, wherein the means for calculating includes means for executing the matrix formula $$\mu_{ai} = \sum_j \epsilon_j(\lambda i)c_j, (j = \text{each element})(i = 1 \ldots N)$$

where $\mu_{ai}$ is for the wavelength $\lambda i$ and N is at least equal to the number of compounds determined plus 1 for a baseline.

21. The apparatus as in claim 17, wherein the means for determining includes means for calculating concentrations from the matrix $$\begin{bmatrix} \left(\frac{\partial \overline{OD}(x_1)}{\partial d}\right)^2 \\ \cdot \\ \cdot \\ \cdot \\ \left(\frac{\partial \overline{OD}(\lambda_n)}{\partial d}\right)^2 \end{bmatrix} = \begin{bmatrix} \epsilon_{HbO2}(\lambda_1) & \ldots & \epsilon_{H2O}(\lambda_1),1 \\ \cdot & & \cdot \\ \cdot & & \cdot \\ \cdot & & \cdot \\ \epsilon_{HbO2}(\lambda_n) & \ldots & \epsilon_{H2O}(\lambda_n),1 \end{bmatrix} \begin{bmatrix} KC_{HbO2} \\ KC_{Hb} \\ KC_{CyOx} \\ KC_{H2O} \\ KC_{off} \end{bmatrix}$$

where $K = \frac{3\mu_s'}{\ln^2 10}$.

22. The apparatus as in claim 17, wherein the means for determining includes means for calculating concentrations from the matrix $$\begin{bmatrix} \left(\frac{\partial \overline{OD}(x_1)}{\partial d}\right)^2 \\ \cdot \\ \cdot \\ \cdot \\ \left(\frac{\partial \overline{OD}(\lambda_n)}{\partial d}\right)^2 \end{bmatrix} = \begin{bmatrix} \epsilon_{HbO2}(\lambda_1) & \ldots & \epsilon_{H2O}(\lambda_1),1 \\ \cdot & & \cdot \\ \cdot & & \cdot \\ \cdot & & \cdot \\ \epsilon_{HbO2}(\lambda_n) & \ldots & \epsilon_{H2O}(\lambda_n),1 \end{bmatrix} \begin{bmatrix} KC_{HbO2} \\ KC_{Hb} \\ KC_{CyOx} \\ KC_{H2O} \\ KC_{off} \end{bmatrix}$$

where $K = \frac{3\mu_s'}{\ln^2 10}$, and means for calculating changes in concentration from the matrix $$\begin{bmatrix} \Delta t\left(\frac{\partial OD(\lambda_1)}{\partial d}\right)^2 \\ \Delta t\left(\frac{\partial OD(\lambda_2)}{\partial d}\right)^2 \\ \cdot \\ \cdot \\ \cdot \\ \Delta t\left(\frac{\partial OD(\lambda_n)}{\partial d}\right)^2 \end{bmatrix} = \begin{bmatrix} \epsilon_{HbO2}(\lambda_1) & \ldots & \ldots \\ \ldots & \ldots & \ldots \\ \ldots & \ldots & \epsilon_{CyOx}(\lambda_n) \end{bmatrix} \begin{bmatrix} K\Delta_t C_{HbO2} \\ K\Delta_t C_{Hb} \\ K\Delta_t C_{CyOx} \end{bmatrix}.$$

23. The apparatus as in claim 16, wherein the means for ascertaining further includes means for determining changes in concentrations of biochemical components as a function of changes in the square of said derivative, and a molar extinction coefficient.

24. The apparatus as in claim 23, wherein the means for determining includes means for calculating changes in concentrations from the matrix $$\begin{bmatrix} \Delta t \left( \dfrac{\partial OD(\lambda_1)}{\partial d} \right)^2 \\ \Delta t \left( \dfrac{\partial OD(\lambda_2)}{\partial d} \right)^2 \\ \vdots \\ \Delta t \left( \dfrac{\partial OD(\lambda_n)}{\partial d} \right)^2 \end{bmatrix} = \begin{bmatrix} \epsilon_{HbO2}(\lambda_1) & \cdots & \cdots \\ \cdots & \cdots & \cdots \\ \cdots & \cdots & \epsilon_{CyOx}(\lambda_n) \end{bmatrix} \begin{bmatrix} K\Delta_t C_{HbO2} \\ K\Delta_t C_{Hb} \\ K\Delta_t C_{CyOx} \end{bmatrix}$$

25. The apparatus as in claim 15, wherein the means for ascertaining further includes means for determining concentrations of biochemical components as a function of the square of said differences.

26. The apparatus as in claim 15, wherein the means for ascertaining further includes means for determining concentrations of biochemical components as a function of the square of said differences and a molar extinction coefficient.

27. The apparatus as in claim 15, wherein the means for ascertaining further includes means for determining differences in concentrations of biochemical components as a function of the square of said differences and a molar extinction coefficient.

28. An apparatus as in claim 15, wherein said directing means directs radiation at each of the wavelengths in a pulse or sine wave form.

\* \* \* \* \*